United States Patent
Hirai et al.

(10) Patent No.: US 12,338,498 B2
(45) Date of Patent: Jun. 24, 2025

(54) HIGH STEVIOL GLYCOSIDE-CONTAINING STEVIA PLANT AND METHOD FOR SCREENING SAME

(71) Applicant: SUNTORY HOLDINGS LIMITED, Osaka (JP)

(72) Inventors: Tadayoshi Hirai, Kyoto (JP); Kazunari Iwaki, Kanagawa (JP); Kentaro Ochiai, Kyoto (JP); Saori Takeyama, Kanagawa (JP); Katsuro Miyagawa, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 330 days.

(21) Appl. No.: 17/924,547

(22) PCT Filed: May 11, 2021

(86) PCT No.: PCT/JP2021/017956
§ 371 (c)(1),
(2) Date: Nov. 10, 2022

(87) PCT Pub. No.: WO2021/230259
PCT Pub. Date: Nov. 18, 2021

(65) Prior Publication Data
US 2023/0265530 A1     Aug. 24, 2023

(30) Foreign Application Priority Data

May 12, 2020   (JP) .................................. 2020-084133

(51) Int. Cl.
C12Q 1/6895    (2018.01)
A01H 6/14      (2018.01)
A23L 27/30     (2016.01)

(52) U.S. Cl.
CPC .......... *C12Q 1/6895* (2013.01); *A01H 6/1488* (2018.05); *A23L 27/36* (2016.08); *C12Q 2600/13* (2013.01)

(58) Field of Classification Search
CPC .................................................. C12Q 1/6895
See application file for complete search history.

(56) References Cited

U.S. PATENT DOCUMENTS

| | | |
|---|---|---|
| 6,255,557 B1 | 7/2001 | Brandle |
| 2007/0116835 A1 | 5/2007 | Prakash et al. |
| 2011/0183056 A1 | 7/2011 | Morita et al. |
| 2013/0202742 A1 | 8/2013 | Prakash et al. |
| 2014/0187761 A1 | 7/2014 | Morita et al. |
| 2016/0058050 A1 | 3/2016 | Morita et al. |
| 2016/0165780 P1 | 6/2016 | Shock et al. |
| 2017/0283819 A1 | 10/2017 | Markosyan et al. |
| 2018/0077959 A1 | 3/2018 | Morita et al. |
| 2019/0330648 A1 | 10/2019 | Markosyan et al. |
| 2019/0357581 A1 | 11/2019 | Morita et al. |
| 2020/0095597 A1 | 3/2020 | Markosyan et al. |
| 2020/0170209 A1 | 6/2020 | Iwaki et al. |
| 2020/0281141 A1 | 9/2020 | Iwaki et al. |
| 2021/0037864 A1 | 2/2021 | Morita et al. |
| 2021/0207159 A1 | 7/2021 | Markosyan et al. |
| 2021/0246517 A1 | 8/2021 | Hirai et al. |
| 2022/0217933 A1 | 7/2022 | Iwaki et al. |

FOREIGN PATENT DOCUMENTS

| | | |
|---|---|---|
| JP | 2002-034502 A | 2/2002 |
| WO | 99/49724 A1 | 10/1999 |
| WO | 2007/070224 A2 | 6/2007 |
| WO | 2010/038911 A1 | 4/2010 |
| WO | WO 2016/049531 A1 * | 3/2016 |
| WO | 2016/094043 A1 | 6/2016 |
| WO | 2018/124142 A1 | 7/2018 |
| WO | 2019/074089 A1 | 4/2019 |
| WO | 2020/027155 A1 | 2/2020 |

OTHER PUBLICATIONS

Khan et al., "Physical and chemical mutagenesis in *Stevia rebaudiana*: variant generation with higher UGT expression and glycosidic profile but with low photosynthetic capabilities," *Acta Physiol Plant*, vol. 38, No. 1, pp. 1-12, published online Dec. 9, 2015.
Extended European Search Report issued in EP Patent Application No. 21805237.1, dated May 28, 2024.
International Search Report issued in PCT/JP2021/017956, dated Jul. 20, 2021, along with an English translation thereof.

* cited by examiner

*Primary Examiner* — Bratislav Stankovic
(74) *Attorney, Agent, or Firm* — GREENBLUM & BERNSTEIN, P.L.C.

(57) ABSTRACT

A method of screening for a stevia plant with high steviol glycoside content, that includes detecting from the genome of a test stevia plant the presence and/or the absence of the following genetic feature: (1) homozygous for the allele wherein the base at the position corresponding to position 290 of SEQ ID NO: 1 is T, and the presence and/or the absence of the following genetic feature: (2) homozygous or heterozygous for the allele wherein the base at the position corresponding to position 40 of SEQ ID NO: 2 is A.

18 Claims, 1 Drawing Sheet
Specification includes a Sequence Listing.

FIG. 1

GGCAGCCATTGATGATGTTGTTGAATGTGATTAATTTGAATGTTATAAAGAAT
TTGGAAAAGAAAAAGGAGGGGACAAAGTTGATGAAATTAGGGGAGTTATGA
TTATGATGGCCATGGTGATTGTGATGAGTGGCACTATGTAATCTAATATTTGA
AGATATGAGACCACTTGACCATGTTATAATCTTATACAAAATAATTAATCCCTC
ACGGTAATTTTTTTCTAATCCTTAAACTGAAATTTGAAAGTAATTTGAGATAGT
GTTTCCCCTAATTTATGCTTTTAG[T]ATGCATTTATTCTATCATATTTTCTATGAG
AATTGG        (SEQ ID NO:1)

FIG. 2

GATCCAATGGAGGGGGTGATTCAGGTAATAAAAGGCATT[A]GTATGGAATATA
CCAAAACATTGCGATTCGTTATTAGCATGGATCTTTCAAGTAATAAACTTATC
GGAGAAATACCAGTTGAGTTAACTGCCCTTCATGCCTTGG  (SEQ ID NO:2)

FIG. 3

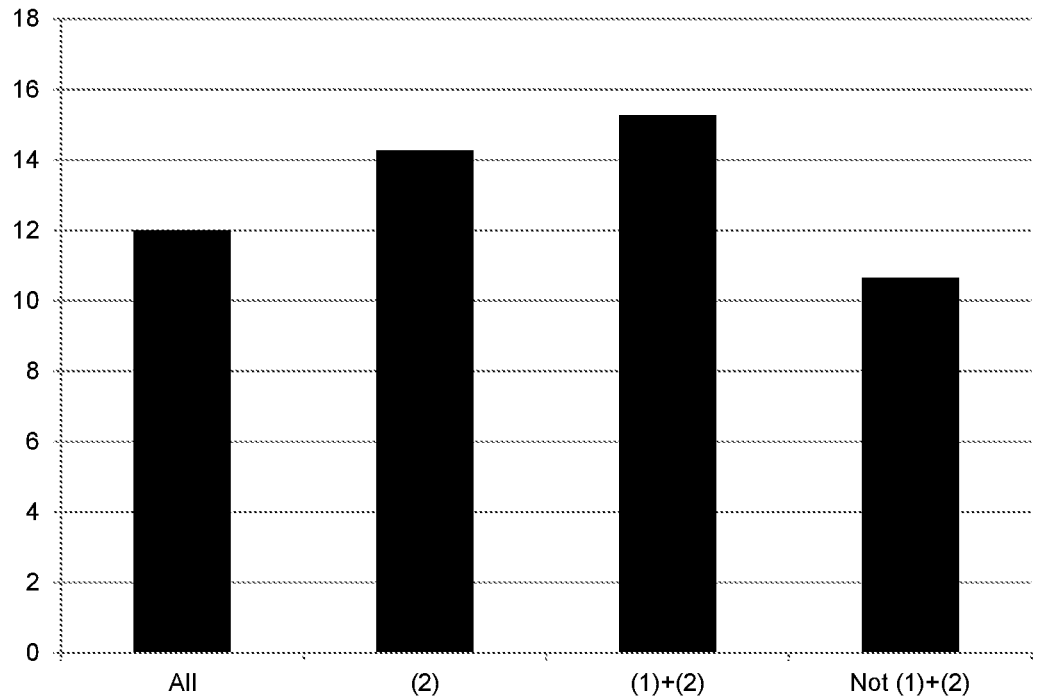

SEQUENCE LISTING

<160> NUMBER OF SEQ ID NOS: 37

<210> SEQ ID NO 1
<211> LENGTH: 326
<212> TYPE: DNA
<213> ORGANISM: Stevia rebaudiana

<400> SEQUENCE: 1

```
ggcagccatt gatgatgttg ttgaatgtga ttaatttgaa tgttataaag aatttggaaa      60
agaaaaagga ggggacaaag ttgatgaaat taggggagtt atgattatga tggccatggt     120
gattgtgatg agtggcacta tgtaatctaa tatttgaaga tatgagacca cttgaccatg     180
ttataatctt atacaaaata attaatccct cacggtaatt tttttctaat ccttaaactg     240
```

```
aaatttgaaa gtaatttgag atagtgtttc ccctaattta tgcttttagt atgcatttat    300
tctatcatat tttctatgag aattgg                                         326

<210> SEQ ID NO 2
<211> LENGTH: 145
<212> TYPE: DNA
<213> ORGANISM: Stevia rebaudiana

<400> SEQUENCE: 2
gatccaatgg aggggggtgat tcaggtaata aaaggcatta gtatggaata taccaaaaca    60
ttgcgattcg ttattagcat ggatctttca agtaataaac ttatcggaga ataccagtt    120 gagttaactg cccttcatgc cttgg                                         145

<210> SEQ ID NO 3
<211> LENGTH: 25
<212> TYPE: DNA
<213> ORGANISM: Artificial Sequence
<220> FEATURE:
<223> OTHER INFORMATION: Synthetic DNA

<400> SEQUENCE: 3
ggcagccatt gatgatgttg ttgaa                                         25

<210> SEQ ID NO 4
<211> LENGTH: 36
<212> TYPE: DNA
<213> ORGANISM: Artificial Sequence
<220> FEATURE:
<223> OTHER INFORMATION: Synthetic DNA

<400> SEQUENCE: 4
ccaattctca tagaaaatat gatagaataa atgcat                             36

<210> SEQ ID NO 5
<211> LENGTH: 21
<212> TYPE: DNA
<213> ORGANISM: Artificial Sequence
<220> FEATURE:
<223> OTHER INFORMATION: Synthetic DNA

<400> SEQUENCE: 5
gatccaatgg aggggggtgat t                                            21

<210> SEQ ID NO 6
<211> LENGTH: 21
<212> TYPE: DNA
<213> ORGANISM: Artificial Sequence
<220> FEATURE:
<223> OTHER INFORMATION: Synthetic DNA

<400> SEQUENCE: 6
ccaaggcatg aagggcagtt a                                             21

<210> SEQ ID NO 7
<211> LENGTH: 21
<212> TYPE: DNA
<213> ORGANISM: Stevia rebaudiana

<400> SEQUENCE: 7
atgcttttag tatgcattta t                                             21

<210> SEQ ID NO 8
<211> LENGTH: 41
```

-continued

```
<212> TYPE: DNA
<213> ORGANISM: Stevia rebaudiana

<400> SEQUENCE: 8
cccctaattt atgcttttag tatgcattta ttctatcata t           41

<210> SEQ ID NO 9
<211> LENGTH: 61
<212> TYPE: DNA
<213> ORGANISM: Stevia rebaudiana

<400> SEQUENCE: 9
gatagtgttt cccctaattt atgcttttag tatgcattta ttctatcata ttttctatga    60
g                                                                   61

<210> SEQ ID NO 10
<211> LENGTH: 21
<212> TYPE: DNA
<213> ORGANISM: Stevia rebaudiana

<400> SEQUENCE: 10
aaaaggcatt agtatggaat a                                             21

<210> SEQ ID NO 11
<211> LENGTH: 41
<212> TYPE: DNA
<213> ORGANISM: Stevia rebaudiana

<400> SEQUENCE: 11
ttcaggtaat aaaaggcatt agtatggaat ataccaaaac a                       41

<210> SEQ ID NO 12
<211> LENGTH: 61
<212> TYPE: DNA
<213> ORGANISM: Stevia rebaudiana

<400> SEQUENCE: 12 gaggggggtga ttcaggtaat aaaaggcatt agtatggaat ataccaaaac attgcgattc   60
g                                                                   61

<210> SEQ ID NO 13
<211> LENGTH: 326
<212> TYPE: DNA
<213> ORGANISM: Stevia rebaudiana

<400> SEQUENCE: 13
ggcagccatt gatgatgttg ttgaatgtga ttaatttgaa tgttataaag aatttggaaa    60
agaaaaagga gggacaaag ttgatgaaat tagggagtt atgattatga tggccatggt    120
gattgtgatg agtggcacta tgtaatctaa tatttgaaga tatgagacca cttgaccatg   180
ttataatctt atacaaaata attaatccct cacggtaatt ttttctaat ccttaaactg    240 aaatttgaaa gtaatttgag atagtgtttc ccctaattta tgcttttagc atgcatttat   300
tctatcatat tttctatgag aattgg                                        326

<210> SEQ ID NO 14
<211> LENGTH: 21
<212> TYPE: DNA
<213> ORGANISM: Stevia rebaudiana

<400> SEQUENCE: 14
```

```
atgcttttag catgcattta t                                            21
```

<210> SEQ ID NO 15
<211> LENGTH: 41
<212> TYPE: DNA
<213> ORGANISM: Stevia rebaudiana

<400> SEQUENCE: 15

```
cccctaattt atgcttttag catgcattta ttctatcata t                      41
```

<210> SEQ ID NO 16
<211> LENGTH: 61
<212> TYPE: DNA
<213> ORGANISM: Stevia rebaudiana

<400> SEQUENCE: 16

```
gatagtgttt cccctaattt atgcttttag catgcattta ttctatcata ttttctatga  60
g                                                                  61
```

<210> SEQ ID NO 17
<211> LENGTH: 145
<212> TYPE: DNA
<213> ORGANISM: Stevia rebaudiana

<400> SEQUENCE: 17

```
gatccaatgg aggggggtgat tcaggtaata aaaggcattc gtatggaata taccaaaaca  60
ttgcgattcg ttattagcat ggatctttca agtaataaac ttatcggaga aataccagtt 120
gagttaactg cccttcatgc cttgg                                       145
```

<210> SEQ ID NO 18
<211> LENGTH: 21
<212> TYPE: DNA
<213> ORGANISM: Stevia rebaudiana

<400> SEQUENCE: 18

```
aaaaggcatt cgtatggaat a                                            21
```

<210> SEQ ID NO 19
<211> LENGTH: 41
<212> TYPE: DNA
<213> ORGANISM: Stevia rebaudiana

<400> SEQUENCE: 19

```
ttcaggtaat aaaaggcatt cgtatggaat ataccaaaac a                      41
```

<210> SEQ ID NO 20
<211> LENGTH: 61
<212> TYPE: DNA
<213> ORGANISM: Stevia rebaudiana

<400> SEQUENCE: 20

```
gagggggtga ttcaggtaat aaaaggcatt cgtatggaat ataccaaaac attgcgattc  60
g                                                                  61
```

<210> SEQ ID NO 21
<211> LENGTH: 25
<212> TYPE: DNA
<213> ORGANISM: Artificial Sequence
<220> FEATURE:
<223> OTHER INFORMATION: Synthetic DNA

<400> SEQUENCE: 21
ggcagccatt gatgatgttg ttgaa                                          25

<210> SEQ ID NO 22
<211> LENGTH: 36
<212> TYPE: DNA
<213> ORGANISM: Artificial Sequence
<220> FEATURE:
<223> OTHER INFORMATION: Synthetic DNA

<400> SEQUENCE: 22
ccaattctca tagaaaatat gatagaataa atgcgt                              36

<210> SEQ ID NO 23
<211> LENGTH: 36
<212> TYPE: DNA
<213> ORGANISM: Artificial Sequence
<220> FEATURE:
<223> OTHER INFORMATION: Synthetic DNA

<400> SEQUENCE: 23
ccaattctca tagaaaatat gatagaataa atgtat                              36

<210> SEQ ID NO 24
<211> LENGTH: 36
<212> TYPE: DNA
<213> ORGANISM: Artificial Sequence
<220> FEATURE:
<223> OTHER INFORMATION: Synthetic DNA

<400> SEQUENCE: 24
ccaattctca tagaaaatat gatagaataa atgcaa                              36

<210> SEQ ID NO 25
<211> LENGTH: 48
<212> TYPE: DNA
<213> ORGANISM: Artificial Sequence
<220> FEATURE:
<223> OTHER INFORMATION: Synthetic DNA

<400> SEQUENCE: 25
ttatttaatg atccaatgga gggggtgatt caggtaataa aaggcact                 48

<210> SEQ ID NO 26
<211> LENGTH: 48
<212> TYPE: DNA
<213> ORGANISM: Artificial Sequence
<220> FEATURE:
<223> OTHER INFORMATION: Synthetic DNA

<400> SEQUENCE: 26
ttatttaatg atccaatgga gggggtgatt caggtaataa aaggctta                 48

<210> SEQ ID NO 27
<211> LENGTH: 48
<212> TYPE: DNA
<213> ORGANISM: Artificial Sequence
<220> FEATURE:
<223> OTHER INFORMATION: Synthetic DNA

<400> SEQUENCE: 27
ttatttaatg atccaatgga gggggtgatt caggtaataa aagtcatg                 48

<210> SEQ ID NO 28
<211> LENGTH: 28
<212> TYPE: DNA

```
<213> ORGANISM: Artificial Sequence
<220> FEATURE:
<223> OTHER INFORMATION: Synthetic DNA

<400> SEQUENCE: 28
tgagggttct caattgattt ccgattgg                                          28

<210> SEQ ID NO 29
<211> LENGTH: 367
<212> TYPE: DNA
<213> ORGANISM: Stevia rebaudiana

<400> SEQUENCE: 29
ttatttaatg atccaatgga gggggtgatt caggtaataa aaggcattag tatggaatat        60
accaaaacat tgcgattcgt tattagcatg gatctttcaa gtaataaact tatcggagaa       120
ataccagttg agttaactgc ccttcatgcc ttggtgagtc tcaatttgtc taataatcat       180
cttattggac acattccgaa tagcattgga aacatgaaag ctttaaattc tctagatttc       240
tcgagaaacg agtaaatgg gttgatccct ccaagcattg gagctttgaa ttttttgagt        300
catttaaatt tgtcaaacaa caacttatca ggaccaattc caatcggaaa tcaattgaga       360
accctca                                                                367

<210> SEQ ID NO 30
<211> LENGTH: 326
<212> TYPE: DNA
<213> ORGANISM: Artificial Sequence
<220> FEATURE:
<223> OTHER INFORMATION: Synthetic DNA

<400> SEQUENCE: 30
ggcagccatt gatgatgttg ttgaatgtga ttaatttgaa tgttataaag aatttggaaa        60
agaaaaagga ggggacaaag ttgatgaaat taggggagtt atgattatga tggccatggt       120
gattgtgatg agtggcacta tgtaatctaa tatttgaaga tatgagacca cttgaccatg       180
ttataatctt atacaaaata attaatccct cacggtaatt ttttctaat ccttaaactg        240 aaatttgaaa gtaatttgag atagtgtttc ccctaattta tgcttttagt acgcatttat       300
tctatcatat tttctatgag aattgg                                            326

<210> SEQ ID NO 31
<211> LENGTH: 290
<212> TYPE: DNA
<213> ORGANISM: Artificial Sequence
<220> FEATURE:
<223> OTHER INFORMATION: Synthetic DNA

<400> SEQUENCE: 31
ggcagccatt gatgatgttg ttgaatgtga ttaatttgaa tgttataaag aatttggaaa        60
agaaaaagga ggggacaaag ttgatgaaat taggggagtt atgattatga tggccatggt       120
gattgtgatg agtggcacta tgtaatctaa tatttgaaga tatgagacca cttgaccatg       180
ttataatctt atacaaaata attaatccct cacggtaatt ttttctaat ccttaaactg        240 aaatttgaaa gtaatttgag atagtgtttc ccctaattta tgcttttagt                  290

<210> SEQ ID NO 32
<211> LENGTH: 36
<212> TYPE: DNA
<213> ORGANISM: Artificial Sequence
<220> FEATURE:
<223> OTHER INFORMATION: Synthetic DNA
```

```
<400> SEQUENCE: 32
acgcatttat tctatcatat tttctatgag aattgg                              36

<210> SEQ ID NO 33
<211> LENGTH: 326
<212> TYPE: DNA
<213> ORGANISM: Artificial Sequence
<220> FEATURE:
<223> OTHER INFORMATION: Synthetic DNA

<400> SEQUENCE: 33
ggcagccatt gatgatgttg ttgaatgtga ttaatttgaa tgttataaag aatttggaaa     60
agaaaaagga ggggacaaag ttgatgaaat taggggagtt atgattatga tggccatggt    120
gattgtgatg agtggcacta tgtaatctaa tatttgaaga tatgagacca cttgaccatg    180
ttataatctt atacaaaata attaatccct cacggtaatt ttttctaat ccttaaactg     240 aaatttgaaa gtaatttgag atagtgtttc ccctaattta tgcttttagc acgcatttat    300
tctatcatat tttctatgag aattgg                                        326

<210> SEQ ID NO 34
<211> LENGTH: 367
<212> TYPE: DNA
<213> ORGANISM: Artificial Sequence
<220> FEATURE:
<223> OTHER INFORMATION: Synthetic DNA

<400> SEQUENCE: 34
ttatttaatg atccaatgga gggggtgatt caggtaataa aaggcactag tatggaatat     60
accaaaacat tgcgattcgt tattagcatg gatctttcaa gtaataaact tatcggagaa    120
ataccagttg agttaactgc ccttcatgcc ttggtgagtc tcaatttgtc taataatcat    180
cttattggac acattccgaa tagcattgga aacatgaaag ctttaaattc tctagatttc    240
tcgagaaacg agttaaatgg gttgatccct ccaagcattg gagctttgaa ttttttgagt    300
catttaaatt tgtcaaacaa caacttatca ggaccaattc caatcggaaa tcaattgaga    360
accctca                                                             367

<210> SEQ ID NO 35
<211> LENGTH: 367
<212> TYPE: DNA
<213> ORGANISM: Artificial Sequence
<220> FEATURE:
<223> OTHER INFORMATION: Synthetic DNA

<400> SEQUENCE: 35
ttatttaatg atccaatgga gggggtgatt caggtaataa aaggcactcg tatggaatat     60
accaaaacat tgcgattcgt tattagcatg gatctttcaa gtaataaact tatcggagaa    120
ataccagttg agttaactgc ccttcatgcc ttggtgagtc tcaatttgtc taataatcat    180
cttattggac acattccgaa tagcattgga aacatgaaag ctttaaattc tctagatttc    240
tcgagaaacg agttaaatgg gttgatccct ccaagcattg gagctttgaa ttttttgagt    300
catttaaatt tgtcaaacaa caacttatca ggaccaattc caatcggaaa tcaattgaga    360
accctca                                                             367

<210> SEQ ID NO 36
<211> LENGTH: 46
<212> TYPE: DNA
```

```
<213> ORGANISM: Artificial Sequence
<220> FEATURE:
<223> OTHER INFORMATION: Synthetic DNA

<400> SEQUENCE: 36
ttatttaatg atccaatgga ggggtgatt caggtaataa aaggca                46

<210> SEQ ID NO 37
<211> LENGTH: 320
<212> TYPE: DNA
<213> ORGANISM: Artificial Sequence
<220> FEATURE:
<223> OTHER INFORMATION: Synthetic DNA

<400> SEQUENCE: 37
ctagtatgga ataccaaa acattgcgat tcgttattag catggatctt tcaagtaata      60
aacttatcgg agaaatacca gttgagttaa ctgcccttca tgccttggtg agtctcaatt   120
tgtctaataa tcatcttatt ggacacattc cgaatagcat tggaaacatg aaagctttaa   180
attctctaga tttctcgaga aacgagttaa atgggttgat ccctccaagc attggagctt   240 tgaattttt gagtcattta aatttgtcaa acaacaactt atcaggacca attccaatcg   300
gaaatcaatt gagaaccctc                                              320
```

HIGH STEVIOL GLYCOSIDE-CONTAINING STEVIA PLANT AND METHOD FOR SCREENING SAME

TECHNICAL FIELD

The present invention relates to a stevia plant with high steviol glycoside content, a screening method therefor, etc.

BACKGROUND ART

In response to consumers' diversified needs, various drinks have been developed and are commercially available. Saccharides such as sucrose are components very commonly blended in drinks for the purpose of, for example, conferring sweetness. However, their influence on health due to excessive consumption has been pointed out. Thus, there are growing needs for lower calorie and naturally derived sweeteners. For example, Patent Literature 1 discloses a functional sweetener composition containing a vitamin, a high intensity sweetener, and a sweetness improving composition.

Steviol glycoside is known as a sweet component contained in a stevia extract. The stevia extract is mainly extracted and purified from a stevia dried leaf. Stevia is a perennial plant of the family Asteraceae with Paraguay in the South America as its place of origin, and its scientific name is *Stevia rebaudiana* Bertoni. Stevia contains a component having approximately 300 or more times the sweetness of sugar and is therefore cultivated for use of this sweet component extracted therefrom as a natural sweetener. The presence of various glycosides such as rebaudioside A (hereinafter, "rebaudioside A" is also abbreviated as "Reb"), RebB, RebC, RebD, RebE and RebD has been reported as steviol glycoside (Patent Literature 2). Among various steviol glycosides, for example, RebA is evaluated as a high intensity sweetener having good quality of sweetness and is widely used. The other steviol glycosides have also been increasingly found to have their unique sweetness and associated taste.

Under these circumstances, a method for screening stevia plant with high sweetening content is known (Patent Literature 3).

CITATION LIST

Patent Literature

Patent Literature 1: WO2007/070224
Patent Literature 2: WO2010/038911
Patent Literature 3: WO2020/027155

SUMMARY OF INVENTION

Technical Problem

There is a need for a stevia plant with high steviol glycoside content.

Means for Solving the Problems

In one aspect, the present invention provides the following.

[1] A method of screening for a high steviol glycoside-content stevia plant, comprising a step of detecting from the genome of a test stevia plant the presence and/or absence of the following genetic feature (1), and the presence and/or the absence of the genetic feature (2).
  (1) Homozygous for the allele wherein the base at the position corresponding to position 290 of SEQ ID NO: 1 is T.
  (2) Homozygous or heterozygous for the allele wherein the base at the position corresponding to position 40 of SEQ ID NO: 2 is A.

[2] The method according to [1], further comprising a step of measuring the content of steviol glycoside in a test stevia plant tissue in which the presence and/or the absence of the genetic features has/have been detected.

[3] The method according to [1] or [2], wherein the steviol glycoside content of the high steviol glycoside-content stevia plant is higher by 3% or more than that of a stevia plant selected by a screening method comprising a step of detecting the presence and/or the absence of the genetic feature (2) but not comprising a step of detecting the presence and/or the absence of the genetic feature (1).

[4] The method according to any one of [1] to [3], wherein the step of detecting the presence and/or the absence of the genetic features is performed by use of dCAPS method or TaqMan PCR method.

[5] A screening kit for a stevia plant with high steviol glycoside content, comprising a reagent for detecting the presence and/or the absence of the following genetic feature (1), and a reagent for detecting the presence and/or the absence of the following genetic feature (2).
  (1) Homozygous for the allele wherein the base at the position corresponding to position 290 of SEQ ID NO: 1 is T.
  (2) Homozygous or heterozygous for the allele wherein the base at the position corresponding to position 40 of SEQ ID NO: 2 is A.

[6] The kit according to [5], wherein the reagent comprises a primer and/or a probe for use in CAPS method, dCAPS method or TaqMan PCR method.

[7] A high steviol glycoside-content stevia plant having the following genetic features (1) and (2).
  (1) Homozygous for the allele wherein the base at the position corresponding to position 290 of SEQ ID NO: 1 is T.
  (2) Homozygous or heterozygous for the allele wherein the base at the position corresponding to position 40 of SEQ ID NO: 2 is A.

[8] The plant according to [7], wherein the plant is a non-genetically modified plant.

[9] The plant according to [7] or [8], wherein the plant includes a stevia plant subjected to a mutagenesis treatment and a progeny plant thereof.

[10] A seed, a tissue, a dried leaf, a tissue culture or a cell of the plant according to any one of [7] to [9].

[11] The tissue, tissue culture or cell according to [10], which is selected from an embryo, a meristem cell, a pollen, a leaf, a root, a root apex, a petal, a protoplast, a leaf section and a callus.

[12] A method of producing a high steviol glycoside-content stevia plant, the method comprising a step of crossing the plant according to any one of [7] to [9] with a second stevia plant.

[13] The method according to [12], wherein the second plant is the plant according to any one of [7] to [9].

[14] A method of producing a high steviol glycoside-content stevia plant, comprising a step of modifying the genome of a stevia plant such that the genome has the following genetic features (1) and (2).

(1) Homozygous for the allele wherein the base at the position corresponding to position 290 of SEQ ID NO: 1 is T.

(2) Homozygous or heterozygous for the allele wherein the base at the position corresponding to position 40 of SEQ ID NO: 2 is A.

[15] The method according to [14], wherein the modification of the genome is performed by a mutagenesis treatment.

[16] An extract of the plant according to any one of [7] to [9], or of the seed, tissue, dried leaf, tissue culture or cell according to or [11], wherein the extract comprises steviol glycoside.

[17] A method of producing an extract comprising a steviol glycoside, comprising a step of obtaining an extract from the plant according to any one of [7] to [9], or from the seed, tissue, dried leaf, tissue culture or cell according to or [11].

[18] A method of producing steviol glycoside, comprising a step of purifying steviol glycoside from the extract according to [16].

[19] A method of producing a food or beverage, a sweetener composition, a flavor or a medicament, comprising:
  a step of providing an extract of the plant according to any one of [7] to [9], an extract of the seed, tissue, dried leaf, tissue culture or cell according to or [11], or the extract according to [16]; and
  a step of adding the extract to a raw material for the food or beverage, sweetener composition, flavor or medicament.

Advantageous Effects of Invention

The present invention enables the obtainment of a stevia plant comprising larger amount of steviol glycoside and the provision of an approach for producing such a plant, a leaf obtainable from such a plant, and a food, a drink, etc. containing Steviol glycoside obtained from this leaf.

BRIEF DESCRIPTION OF DRAWINGS

FIG. 1 is a diagram showing the position of the base related to the genetic feature (1) in the nucleotide sequence of SEQ ID NO: 1. The boxed base is a base related to the genetic feature (1).

FIG. 2 is a diagram showing the position of the base related to the genetic feature (2) in the nucleotide sequence of SEQ ID NO: 2. The boxed base is a base related to the genetic feature (2).

FIG. 3 is graph showing an average TSG content (%) in dried leaves of individual groups having various genetic features in population A. "All" represents all the individuals of the population A, "(2)" represents an individual having the genetic feature (2), "(1)+ (2)" represents an individual having the genetic features of the present invention, and "Not (1)+ (2)" represents an individual that does not have the genetic features of the present invention.

DESCRIPTION OF EMBODIMENTS

Hereinafter, the present invention will be described in detail. The embodiments are given below merely for illustrating the present invention and are not intended to limit the present invention by such embodiments. The present invention can be carried out in various modes without departing from the spirit of the present invention.

Note that all documents, as well as laid-open application publications, patent application publications, and other patent documents cited herein shall be incorporated herein by reference. The present specification incorporates the contents of the specification and the drawings of Japanese Patent Application No. 2020-084133, filed on May 12, 2020, from which the present application claims priority.

1. Stevia Plant with High Steviol Glycoside Content

In one aspect, the present invention provides a stevia plant with high Steviol glycoside content having the following genetic features (1) and (2) (hereinafter, may be referred to as the "plant of the present invention").

(1) Homozygous for the allele wherein the base at the position corresponding to position 290 of SEQ ID NO: 1 is T.

(2) Homozygous or heterozygous for the allele wherein the base at the position corresponding to position 40 of SEQ ID NO: 2 is A.

The plant of the present invention is a species derived from a stevia plant of wild species and has acquired the genetic features (1) and (2), which result in an increase of the Steviol glycoside content (hereinafter, the combination of the above genetic features (1) and (2) may be generically referred to as the "genetic features of the present invention").

The phrase "position corresponding to" means the following. In case a sequence identical to a reference sequence (e.g., SEQ ID NO: 1, etc.) is present in the genome, it means a position in the sequence (e.g., 290, 40, etc.) present in the genome, and in case a sequence identical to the reference sequence is not present in the genome, it means a position in a sequence in the genome corresponding to the reference sequence, which corresponds to the position in the reference sequence. Whether or not a sequence identical to or corresponding to the reference sequence exists in the genome can be determined by, for example, amplifying genomic DNA of the stevia plant of interest with a primer capable of amplifying the reference sequence by PCR, sequencing the amplified product, and performing alignment analysis between the obtained sequence and the reference sequence. Non-limiting examples of a sequence corresponding to a reference sequence include, for example, a nucleotide sequence having a sequence identity of 60% or more, 70% or more, 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 98.1% or more, 98.4% or more, 98.7% or more, 99% or more, 99.2% or more, 99.5% or more, or 99.8% or more to the reference sequence. The position corresponding to the position in the reference sequence in the sequence corresponding to the reference sequence in the genome can be determined by taking into account the nucleotide sequence before and after the position in the reference sequence and the like. For example, a position in the sequence corresponding to the reference sequence in the genome corresponding to a position in the reference sequence can be determined by an alignment analysis of a reference sequence with a sequence corresponding to a reference sequence in the genome.

For instance, when taking "the position corresponding to position 290 of SEQ ID NO: 1" of the genetic feature (A) of the present invention as an example, in case the genome of a stevia plant has a portion consisting of a nucleotide sequence identical to SEQ ID NO: 1, "the position corresponding to position 290 of SEQ ID NO: 1" is position 290 from the 5' end of the portion consisting of a nucleotide sequence identical to SEQ ID NO: 1 in the genome. On the other hand, in case the genome of a stevia plant has a portion consisting of a nucleotide sequence which is not identical to, but which corresponds to SEQ ID NO: 1, the genome does not have a portion consisting of a nucleotide sequence identical to SEQ ID NO: 1. Therefore, "the position corresponding to position 290 of SEQ ID NO: 1" does not necessarily correspond to position 290 from the 5' end of the portion corresponding to SEQ ID NO: 1. However, it is possible to identify "the position corresponding to position 290 of SEQ ID NO: 1" in the genome of such a stevia plant by taking into account the nucleotide sequence before and after the position 290 of SEQ ID NO: 1, and the like. For instance, one can identify "the position corresponding to position 290 of SEQ ID NO: 1" in the genome of a stevia plant by an alignment analysis of the nucleotide sequence of a portion corresponding to SEQ ID NO: 1 in the genome of a stevia plant and the nucleotide sequence of SEQ ID NO: 1.

"The portion consisting of a nucleotide sequence corresponding to SEQ ID NO: 1" means, for instance, a portion consisting of a nucleotide sequence having a sequence identity of 60% or more, 70% or more, 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 98.1% or more, 98.4% or more, 98.7% or more, 99% or more, 99.2% or more, 99.5% or more, or 99.8% or more to the nucleotide sequence of SEQ ID NO: 1.

In some embodiments, "the portion consisting of a nucleotide sequence corresponding to SEQ ID NO: 1" includes a portion of the genome of a stevia plant which can be amplified by PCR using a forward primer (e.g., the one having the sequence of SEQ ID NO: 3) which hybridizes to a complementary sequence of a portion of positions 1 to 289 from the 5' end of SEQ ID NO: 1 (i.e., from the 5' end of SEQ ID NO: 1 to the base upstream by one base relative to the position 290 which relates to the genetic feature (1)) and a reverse primer (e.g., the one having the sequence of SEQ ID NO: 4) which hybridizes to a portion of positions 1 to 36 from the 3' end of SEQ ID NO: 1 (i.e., from the 3' end of SEQ ID NO: 1 to the base downstream by one base relative to the position 290 which relates to the genetic feature (1)).

In some embodiments, "the portion consisting of a nucleotide sequence corresponding to SEQ ID NO: 2" includes a portion of the genome of a stevia plant which can be amplified by PCR using a forward primer (e.g., the one having the sequence of SEQ ID NO: 5) which hybridizes to a complementary sequence of a portion of positions 1 to 39 from the 5' end of SEQ ID NO: 2 (i.e., from the 5' end of SEQ ID NO: 2 to the base upstream by one base relative to the position 40 which relates to the genetic feature (2)) and a reverse primer (e.g., the one having the sequence of SEQ ID NO: 6) which hybridizes to a portion of positions 1 to 105 from the 3' end of SEQ ID NO: 2 (i.e., from the 3' end of SEQ ID NO: 2 to the base downstream by one base relative to the position 40 which relates to the genetic feature (2)).

In a specific embodiment, "the portion consisting of a nucleotide sequence corresponding to SEQ ID NO: 1" includes, for instance, a portion of the genome of a stevia plant which can be amplified by PCR using a forward primer comprising the nucleotide sequence of SEQ ID NO: 3 and a reverse primer comprising the nucleotide sequence of SEQ ID NO: 4.

In a specific embodiment, "the portion consisting of a nucleotide sequence corresponding to SEQ ID NO: 2" includes, for instance, a portion of the genome of a stevia plant which can be amplified by PCR using a forward primer comprising the nucleotide sequence of SEQ ID NO: 5 and a reverse primer comprising the nucleotide sequence of SEQ ID NO: 6.

In a specific embodiment, "the allele wherein the base at the position corresponding to position 290 of SEQ ID NO: 1 is T" (hereinafter, may be referred to as "allele related to the genetic feature (1)") comprises the nucleotide sequence of SEQ ID NO: 1, 7, 8 or 9.

In a specific embodiment, "the allele wherein the base at the position corresponding to position 40 of SEQ ID NO: 2 is A" (hereinafter, may be referred to as "allele related to the genetic feature (2)") comprises the nucleotide sequence of SEQ ID NO: 2, 10, 11 or 12.

Here, (1) the position corresponding to position 290 of SEQ ID NO: 1 and (2) the position corresponding to position 40 of SEQ ID NO: 2 may be generically referred to as a "polymorphic site of the present invention" or a "site related to the genetic feature of the present invention".

The above genetic features can be detected by PCR method, TaqMan PCR method, sequencing method, microarray method, Invader method, TILLING method, RAD (random amplified polymorphic DNA) method, restriction fragment length polymorphism (RFLP) method, PCR-SSCP method, AFLP (amplified fragment length polymorphism) method, SSLP (simple sequence length polymorphism) method, CAPS (cleaved amplified polymorphic sequence) method, dCAPS (derived cleaved amplified polymorphic sequence) method, allele-specific oligonucleotide (ASO) method, ARMS method, denaturing gradient gel electrophoresis (DGGE) method, CCM (chemical cleavage of mismatch) method, DOL method, MALDI-TOF/MS method, TDI method, padlock probe method, molecular beacon method, DASH (dynamic allele specific hybridization) method, UCAN method, ECA method, PINPOINT method, PROBE (primer oligo base extension) method, VSET (very short extension) method, Survivor assay, Sniper assay, Luminex assay, GOOD method, LCx method, SNAPshot method, Mass ARRAY method, pyrosequencing method, SNP-IT method, melting curve analysis method, etc., but detection methods are not limited thereto. Details for the detection method of a genetic variation are mentioned below.

In a specific embodiment, each genetic feature of the present invention is detectable by dCAPS method using the following combination of a primer set and a restriction enzyme.

In case a candidate plant has the genetic feature (1), for example, a band of approximately 290 bp long (e.g., SEQ ID NO: 31) and a band of approximately 36 bp long (e.g., SEQ ID NO: 32) are obtained by: performing PCR amplification using a forward primer having the nucleotide sequence shown in SEQ ID NO: 21 and a reverse primer having the nucleotide sequence shown in SEQ ID NO: 22 on the genomic DNA of the candidate plant; and treating the obtained PCR product (approximately 326 bp long, e.g., SEQ ID NO: 30) with a restriction enzyme RsaI. On the other hand, in case the candidate plant does not have the genetic feature (1), a PCR product of approximately 326 bp long (e.g., SEQ ID NO: 33 or SEQ ID NOs: 30 and 33) is formed by performing PCR amplification in the same way as above, and when the PCR product is treated with the restriction enzyme, an uncleaved PCR product of approximately 326 bp long (e.g., SEQ ID NO: 33) is found.

In case a candidate plant has the genetic feature (2), for example, a band of approximately 46 bp long (e.g., SEQ ID NO: 36) and a band of approximately 320 bp long (e.g., SEQ ID NO: 37) are obtained by: performing PCR amplification using a forward primer having the nucleotide sequence shown in SEQ ID NO: 25 and a reverse primer having the nucleotide sequence shown in SEQ ID NO: 28 on the genomic DNA of the candidate plant; and treating the obtained PCR product (approximately 367 bp long, e.g., SEQ ID NO: 34 or SEQ ID NOs: 34 and 35) with a restriction enzyme RsaI. On the other hand, in case the candidate plant does not have the genetic feature (2), a PCR product of approximately 367 bp long (e.g., SEQ ID NO: 35) is formed by performing PCR amplification in the same way as above, and when the PCR product is treated with the restriction enzyme, only an uncleaved PCR product of approximately 367 bp long (e.g., SEQ ID NO: 35) is found.

The plant of the present invention is a species derived from a stevia plant of wild species and has acquired the above genetic features which result in an increase of the Steviol glycoside content. The genetic features may be the ones generated by a genetic modification approach or the ones generated by a non-genetic modification approach. Therefore, the plant of the present invention may be the one obtained by a genetic modification approach or a progeny thereof (hereinafter, may be referred to as "genetically modified plant") or the one obtained by a non-genetic modification approach or a progeny thereof (hereinafter, may be referred to as "non-genetically modified plant").

Herein, examples of the "non-genetic modification approach" include a method of inducing a variation in the gene of a host cell (or a host plant) without transfection with a foreign gene. Examples of such a method include a method of allowing a mutagen to act on a plant cell. Examples of such a mutagen include ethyl methanesulfonate (EMS) and sodium azide. For example, EMS can be used at a concentration such as 0.1%, 0.2%, 0.3%, 0.4%, 0.5%, 0.6%, 0.7%, 0.8%, 0.9%, or 1.0% to treat a plant cell. The treatment time is about 1 hour to about 48 hours, about 2 hours to about 36 hours, about 3 hours to about 30 hours, about 4 hours to about 28 hours, about 5 hours to about 26 hours, or about 6 hours to about 24 hours. The procedures themselves of the treatment are known in the art and can be performed by dipping a water-absorbed seed obtained through a water absorption process in a treatment solution containing the mutagen at the concentration described above for the treatment time described above.

Another example of the non-genetic modification approach includes a method of irradiating a plant cell with radiation or light beam such as X-ray, y ray, or ultraviolet ray. In the case of irradiation with ultraviolet ray, a cell irradiated using an appropriate dose (ultraviolet lamp intensity, distance, and time) of ultraviolet ray is cultured in a selective medium or the like, and then, a cell, a callus, or a plant having the trait of interest can be selected. In this operation, the irradiation intensity may be 0.01 to 100 Gr, 0.03 to 75 Gr, 0.05 to 50 Gr, 0.07 to 25 Gr, 0.09 to 20 Gr, 0.1 to 15 Gr, 0.1 to 10 Gr, 0.5 to 10 Gr, or 1 to 10 Gr. The irradiation distance may be 1 cm to 200 m, 5 cm to 100 m, 7 cm to 75 m, 9 cm to 50 m, 10 cm to 30 m, 10 cm to 20 m, or 10 cm to 10 m. The irradiation time may be 1 minute to 2 years, 2 minutes to 1 year, 3 minutes to 0.5 years, 4 minutes to 1 month, 5 minutes to 2 weeks, or 10 minutes to 1 week. The irradiation intensity, distance and time differ depending on the type of radiation or light beam, or the state of the subject to be irradiated (cell, callus, or plant) and can be appropriately adjusted by those skilled in the art.

Approaches such as cell fusion, anther culture (haploid induction), and remote crossing (haploid induction) are also known in the art.

In general, plant cells may involve a mutation during culture. Therefore, it is preferred to regenerate a plant individual, for more stably maintaining the trait.

The scope of the present invention does not exclude a plant obtained by the ex-post facto genetic recombination (e.g., genome editing) with a non-genetically modified stevia plant as a host (e.g., a plant further provided with another trait by genetic recombination with the plant of the present invention as a host).

The plant of the present invention is of high Steviol glycoside content type. The stevia plant with a high Steviol glycoside content means that the Steviol glycoside content is high as compared with a stevia plant that does not have the genetic features of the present invention. The high Steviol glycoside content means that, for example, the average or median Steviol glycoside content of a population of the plants of the present invention is higher than that of a population of stevia plants that do not have the genetic features of the present invention, and/or is higher than that of a population of stevia plants having the genetic features (2).

In some embodiments, the average Steviol glycoside content of the population of the plants of the present invention is higher by about 10% or more, about 11% or more, about 12% or more, about 13% or more, about 14% or more, about 15% or more, about 16% or more, about 17% or more, about 18% or more, about 19% or more, about 20% or more, about 21% or more, about 22% or more, about 23% or more, about 24% or more, about 25% or more, about 26% or more, about 27% or more, about 28% or more, about 29% or more, about 30% or more, about 31% or more, about 32% or more, about 33% or more, about 34% or more, about 35% or more, about 36% or more, about 37% or more, about 38% or more, about 39% or more, about 40% or more, about 41% or more, about 42% or more, about 43% or more, about 43.5% or more, about 44% or more, about 45% or more, about 46% or more, about 47% or more, about 48% or more, about 49% or more 又は about 50% or more than that of a population of stevia plants that do not have the genetic features of the present invention.

In some embodiments, the average Steviol glycoside content of the population of the plants of the present invention is higher by about 1.0% or more, about 1.3% or more, about 1.5% or more, about 1.8% or more, about 2.0% or more, about 2.3% or more, about 2.5% or more, about 2.8% or more, about 3.0% or more, about 3.3% or more, about 3.5% or more, about 3.8% or more, about 4.0% or more, about 4.3% or more, about 4.5% or more, about 4.8% or more, about 5.0% or more, about 5.3% or more, about 5.5% or more, about 5.8% or more, about 6.0% or more, about 6.3% or more, about 6.5% or more, about 6.8% or more, about 7.0% or more, about 7.2% or more, about 7.5% or more, about 7.8% or more, about 8.0% or more, about 8.3% or more, about 8.5% or more, about 8.8% or more, about 9.0% or more, about 9.3% or more, about 9.5% or more, about 9.8% or more 又は about 10.0% or more than that of a population of stevia plants having the genetic features (2).

The steviol glycoside is a generic name for compounds having a steviol backbone conjugated to a sugar such as glucose, rhamnose, or xylose, and includes, for example, RebA, RebB, RebC, RebD, RebE, RebF, RebG, RebI, RebJ, RebK, RebN, RebM, RebO, RebQ, RebR, dulcoside A, rubusoside, steviolmonoside, steviolbioside and stevioside.

In one embodiment, the steviol glycoside includes one or more glycosides selected from RebA, RebB, RebC, RebD, RebE, RebF, RebI, RebJ, RebK, RebN, RebM, RebO, RebQ, RebR, dulcoside A, rubusoside, steviolmonoside, steviolbioside and stevioside. In a specific embodiment, the steviol glycoside comprises RebA, RebB, RebC, RebD, RebE, RebF, RebG, RebM, RebN and stevioside, or is selected from these steviol glycosides.

The total steviol glycoside (TSG) is a generic name for measurable steviol glycosides and includes neither an unknown steviol glycoside nor a steviol glycoside present at a level less than the detection limit. Preferably, the TSG is any combination of two or more members selected from the group consisting of RebA, RebB, RebC, RebD, RebE, RebF, RebG, RebI, RebJ, RebK, RebM, RebN, RebO, RebQ, RebR, dulcoside A, rubusoside, steviolmonoside, steviolbioside and stevioside. In a specific embodiment, the TSG consists of the combination of RebA, RebB, RebC, RebD, RebE, RebF, RebG, RebM, RebN and stevioside.

The steviol glycoside can be extracted in the state of a liquid extract by reacting a fresh leaf or a dried leaf of the plant of the present invention with a suitable solvent (an aqueous solvent such as water or an organic solvent such as an alcohol, ether or acetone). For the extraction conditions, etc., see a method described in Ohta et al., J. Appl. Glycosci., Vol. 57, No. 3, 199-209 (2010) or WO2010/038911, or a method described in Examples mentioned later. The dried leaf refers to a leaf having a water content decreased to 10% by weight or less, 7% by weight or less, 5% by weight or less, 4% by weight or less, 3% by weight or less, 2% by weight or less or 1% by weight or less by drying a fresh leaf.

Preferably, the water content of the dried leaf of the plant of the present invention is 3 to 4% by weight. Steviol glycoside can be further purified from the liquid extract thus obtained by use of a method known in the art such as a gradient of ethyl acetate or any of other organic solvents: water, high performance liquid chromatography (HPLC), gas chromatography, time-of-flight mass spectrometry (TOF-MS), or ultra (high) performance liquid chromatography (UPLC).

The contents of the steviol glycoside relating to the present invention can be measured by a method described in Ohta et al., supra or WO2010/038911, or a method described in Examples mentioned later. Specifically, for instance, a fresh leaf can be sampled from the stevia plant of the present invention, followed by measurement by LC-MS/MS and the like.

The plant of the present invention may include not only the whole plant but a plant organ (e.g., a leaf, a petal, a stem, a root, and a seed), a plant tissue (e.g., epidermis, phloem, soft tissue, xylem, vascular bundle, palisade tissue, and spongy tissue), various forms of plant cells (e.g., suspended cultured cells), a protoplast, a leaf section, a callus, and the like. The leaf may be a dried leaf.

The plant of the present invention may also include a tissue culture or a cultured plant cell. This is because the plant can be regenerated by culturing such a tissue culture or a cultured plant cell.

Examples of a regenerable form of the plant of the present invention include, but are not limited to, embryos, meristem cells, pollens, leaves, roots, root apices, petals, protoplasts, leaf sections and calluses.

2. Method of Producing Plant of Present Invention

In an alternative aspect, the present invention provides a method of producing a high steviol glycoside-content stevia plant, the method comprising a step of crossing the stevia plant of the present invention with a second stevia plant (hereinafter, referred to as the "production method of the present invention").

The "high steviol glycoside-content stevia plant" produced by the method has the same phenotype and genetic features as those of the plant of the present invention.

Specifically, the phenotype of the plant produced by the production method of the present invention is the phenotype of high steviol glycoside content type described in the section relating to the plant of the present invention. The genetic feature of the plant produced by the production method of the present invention is having the genetic features of the present invention. Methods for detecting these genetic features are as mentioned above and later.

In the production method of the present invention, "hybridizing" means that the plant of the present invention is crossed with a second plant to obtain a progeny plant thereof (plant produced by the production method of the present invention. The hybridizing method is preferably backcross. The "backcross" is an approach of further crossing a progeny plant generated between the plant of the present invention and the second plant, with the plant of the present invention (i.e., a plant having the genetic feature(s) of the present invention) to produce a plant having the genetic feature(s) of the present invention. When the second plant for use in the production method of the present invention has the same phenotype and genetic features as those of the plant of the present invention, the crossing is substantially backcross. Hybridization is preferably performed over two generations or more, but in case where the genetic feature is heterozygous, etc., a plant having a desired combination of genetic features may be obtained in one generation.

Alternatively, the plant of the present invention can also be produced by selfing. The selfing can be performed by the self-pollination of the stamen pollen of the plant of the present invention with the pistil of the plant of the present invention.

Since the plant produced by the production method of the present invention has the same phenotype and genetic features as those of the plant of the present invention, the plant produced by the production method of the present invention can be further crossed with a third stevia plant to produce a high steviol glycoside-content stevia plant.

In an alternative embodiment, the plant of the present invention may be produced by regenerating a plant by the culture of the tissue culture or the cultured plant cell mentioned above. The culture conditions are the same as those for culturing a tissue culture or a cultured plant cell of the wild type stevia plant and are known in the art (Protocols for in vitro cultures and secondary metabolite analysis of aromatic and medicinal plants, Method in molecular biology, vol. 1391, pp. 113-123).

In a further alternative embodiment, the plant of the present invention may be produced by modifying the genome of a stevia plant so that the stevia plant is allowed to acquire the genetic features of the present invention. The acquirement of the genetic features of the present invention may be performed by a genetic modification approach or may be performed by a non-genetic modification approach. Examples of the non-genetic modification approach include mutagenesis treatment such as treatment with a mutagen and treatment by irradiation with radiation or light beam described in the section relating to the plant of the present invention. Specifically, for example, the genetic features of the present invention can be provided: to an individual having the allele wherein the base at the position corresponding to position 290 of SEQ ID NO: 1 is not T (e.g., the allele wherein the base at this position is C), by the substitution of the base at this position with T; to an individual having the allele wherein the base at the position corresponding to position 40 of SEQ ID NO: 2 is not A (e.g., the allele wherein the base at this position is C), by the substitution of the base at this position with A.

3. Method of Screening for Plant of Present Invention

The plant of the present invention or the plant having the same phenotype and/or genetic feature as those of the plant of the present invention can be screened for by detecting the genetic feature(s) of the present invention from a tissue of a test plant. In this context, "screening" means that the plant of the present invention is discriminated from the other plants to select the plant of the present invention.

Thus, in another aspect, the present invention provides a method of screening for a high steviol glycoside-content stevia plant, comprising a step of detecting the presence and/or the absence of the genetic features (1) of the present invention and the presence and/or the absence of the genetic features (2) of the present invention from the genome of a test stevia plant (hereinafter, may be referred to as the "screening method of the present invention").

The screening method of the present invention may further comprise a step of selecting from among the test plants a plant in which the presence of at least one genetic feature of the above is detected.

The presence of the genetic features of the present invention can be determined, for example, by:
  detecting the presence of only an allele wherein the base at the position corresponding to position 290 of SEQ ID NO: 1 is T (e.g., an allele comprising the nucleotide sequence of SEQ ID NO: 1, 7, 8 or 9);
  detecting the presence of an allele wherein the base at the position corresponding to position 40 of SEQ ID NO: 2 is A (e.g., an allele comprising the nucleotide sequence of SEQ ID NO: 2, 10, 11 or 12); and/or
  detecting the absence of an allele wherein the base at the position corresponding to position 290 of SEQ ID NO: 1 is C (e.g., an allele comprising the nucleotide sequence of SEQ ID NO: 13, 14, 15 or 16).

The absence of the genetic features of the present invention can be determined, for example, by detecting the absence of an allele selected from the group consisting of:
  an allele wherein the base at the position corresponding to position 290 of SEQ ID NO: 1 is T (e.g., an allele comprising the nucleotide sequence of SEQ ID NO: 1, 7, 8 or 9); and
  an allele wherein the base at the position corresponding to position 40 of SEQ ID NO: 2 is A (e.g., an allele comprising the nucleotide sequence of SEQ ID NO: 2, 10, 11 or 12); and/or detecting the presence of:
  an allele wherein the base at the position corresponding to position 290 of SEQ ID NO: 1 is C (e.g., an allele comprising the nucleotide sequence of SEQ ID NO: 13, 14, 15 or 16).

Specific examples of methods of detecting the variations of the present invention include, but not limited to, PCR method, TaqMan PCR method, sequencing method, microarray method, Invader method, TILLING method, RAD method, RFLP method, PCR-SSCP method, AFLP method, SSLP method, CAPS method, dCAPS method, ASO method, ARMS method, DGGE method, CCM method, DOL method, MALDI-TOF/MS method, TDI method, padlock probe method, molecular beacon method, DASH method, UCAN method, ECA method, PINPOINT method, PROBE method, VSET method, Survivor assay, Sniper assay, Luminex assay, GOOD method, LCx method, SNAPshot method, Mass ARRAY method, pyrosequencing method, SNP-IT method, melting curve analysis method, etc.

In the case of PCR method, it is preferable to generate a primer such that the 3' end portion has a sequence complementary to the site related to the genetic feature of the present invention. By using a primer designed in this way, the polymerase extension reaction proceeds because the primer hybridizes completely to the template if the template sample has the allele related to the genetic feature of the present invention, whereas if the template does not have the allele related to the genetic feature of the present invention, the extension reaction does not occur because the nucleotide at the 3' end of the primer mismatches the template. Therefore, PCR amplification is performed using such a primer, and the amplification product is analyzed by agarose gel electrophoresis or the like, and if an amplification product of a predetermined size can be confirmed, the template as the sample has the allele related to the genetic feature of the present invention, and if the amplification product is not present, it can be judged that the template does not have the allele related to the genetic feature of the present invention.

Alternatively, the genetic feature(s) of the present invention can be detected by designing the primer sequence so that the site related to the genetic feature of the present invention and the primer sequence do not overlap and a nucleotide fragment comprising the allele related to the genetic feature of the present invention can be PCR amplified, and by sequencing the nucleotide sequence of the amplified nucleotide fragment.

For PCR and agarose gel electrophoresis see Sambrook, Fritsch and Maniatis, "Molecular Cloning: A Laboratory Manual" 2nd Edition (1989), Cold Spring Harbor Laboratory Press.

TaqMan PCR method uses fluorescently labeled allele-specific oligos and Taq DNA polymerases (Livak, K. J. Genet. Anal. 14, 143 (1999); Morris T. et al., J. Clin. Microbiol. 34, 2933 (1996)).

The sequencing method is a method of analyzing the presence or absence of the genetic feature by amplifying a region containing the site related to the genetic feature by PCR and sequencing the DNA sequence using a Dye Terminator or the like (Sambrook, Fritsch and Maniatis, "Molecular Cloning: A Laboratory Manual" 2nd Edition (1989), Cold Spring Harbor Laboratory Press).

A DNA microarray is one in which one end of a nucleotide probe is immobilized in an array on a support, and includes a DNA chip, a Gene chip, a microchip, a bead array, and the like. By using a probe containing a sequence complementary to a sequence comprising the genetic feature of the present invention, the presence or absence of the genetic feature of the present invention can be comprehensively detected. DNA microarray assays such as DNA chips include GeneChip assays (see Affymetrix; U.S. Pat. Nos. 6,045,996; 5,925,525; and 5,858,659). The GeneChip technique utilizes a miniaturized, high density microarray of oligonucleotide probes affixed to a chip.

The invader method combines the hybridization of two reporter probes specific for each allele having or not having the genetic feature such as SNPs and one invader probe to template DNA and the cleavage of DNA by Cleavase enzyme with a special endonuclease activity which cleaves a DNA by recognizing its structure (Livak, K. J. Biomol. Eng. 14, 143-149 (1999); Morris T. et al., J. Clin. Microbiol. 34, 2933 (1996); Lyamichev, V. et al., Science, 260, 778-783 (1993), and the like).

TILLING (Targeting Induced Local Lesions IN Genomes) method is a method in which mutational mismatches in the genomes of a mutagenized mutant population are screened by PCR-amplification and CEL I nuclease-treatment.

In one embodiment, the genetic feature (1) of the present invention can be detected, for example, by dCAPS method using the following primer set and a restriction enzyme.

Primer Set:

A primer set comprising a forward primer comprising a sequence (e.g., SEQ ID NO: 21) of any continuous sequence of 15 bases or more which is positioned upstream of the position 289 of SEQ ID NO: 1 and a reverse primer comprising a continuous sequence of 15 to 36-base long from the 3' end of the sequence selected from SEQ ID NOs: 22 to 24.

Restriction Enzyme:

A restriction enzyme for the primer set based on SEQ ID NO: 22 includes RsaI, a restriction enzyme for the primer set based on SEQ ID NO: 23 includes SnaI, and a restriction enzyme for the primer set based on SEQ ID NO: 24 includes AluI.

In one embodiment, the genetic feature (2) of the present invention can be detected, for example, by dCAPS method using the following primer set and a restriction enzyme.

Primer Set:

A primer set comprising a forward primer comprising a continuous sequence of 15 to 48-base long from the 3' end of the sequence selected from SEQ ID NOs: 25 to 27 and a reverse primer comprising a sequence (e.g., SEQ ID NO: 28) complementary to any continuous sequence of 15 bases or more which is positioned downstream of the position 49 of SEQ ID NO: 29.

Restriction Enzyme:

A restriction enzyme for the primer set based on SEQ ID NO: 25 includes SpeI or MaeI, a restriction enzyme for the primer set based on SEQ ID NO: 26 includes AflII/MseI, and a restriction enzyme for the primer set based on SEQ ID NO: 27 includes BspHI.

The sequences of the primers can be optimized within a range that satisfies the conditions described above. For the optimization of primer design, see, for example, Sambrook and Russell, "Molecular Cloning: A Laboratory Manual" 3rd Edition (2001), Cold Spring Harbor Laboratory Press. Each of the primers may be 15 to 50-base long, 18 to 48-base long, 20 to 45-base long, 30 to 40-base long, or the like. The restriction enzyme for each primer set also includes other enzymes that recognize the same sequence and cleave the same site as in the above enzyme, or an isoschizomer of the above enzyme. It is also possible to design a primer set other than those described above on the basis of the genetic feature(s) of the present invention and select a restriction enzyme appropriate therefor.

In a specific embodiment, the genetic features of the present invention can be detected, e.g., by dCAPS method using the primer set having the following sequence and restriction enzyme.

TABLE 1

Examples of combination of primer set and restriction enzyme for detecting genetic feature (1)

| Forward primer | Reverse primer | Restriction enzyme |
|---|---|---|
| SEQ ID NO: 21 | SEQ ID NO: 22 | RsaI |
| SEQ ID NO: 21 | SEQ ID NO: 23 | SnaI |
| SEQ ID NO: 21 | SEQ ID NO: 24 | AluI |

TABLE 2

Examples of combination of primer set and restriction enzyme for detecting genetic feature (2)

| Forward primer | Reverse primer | Restriction enzyme |
|---|---|---|
| SEQ ID NO: 25 | SEQ ID NO: 28 | SpeI/MaeI |
| SEQ ID NO: 26 | SEQ ID NO: 28 | AflII/MseI |
| SEQ ID NO: 27 | SEQ ID NO: 28 | BspHI |

The combinations of the primer set and the restriction enzyme described above are mere examples, and other combinations of primer sets and restriction enzymes capable of detecting the genetic feature(s) of the present invention can be found by those skilled in the art.

The screening methods of the present invention may further comprise a step of determining the content of steviol glycoside (e.g., the content of TSG) of the test stevia plant tissue (e.g., a leave) for which the genetic features of the present invention have been detected. The determination of the content of steviol glycoside is as described in the section relating to the plant of the present invention. In this embodiment, the screening method of the present invention may be applied to daughter plants obtained by selecting individuals with a higher steviol glycoside content from among the test stevia plants in which the genetic features of the present invention is/are detected, and crossing the selected individuals with another stevia plants. Thus, the screening method of the present invention may comprise one or more of the following steps.

(i) Detecting the genetic features of the present invention from the genome of a test stevia plant;

(ii) determining the content of steviol glycoside of the test stevia plant tissue in which the genetic features of the present invention have been detected;

(iii) selecting an individual with a higher steviol glycoside content from among the test stevia plants in which the genetic features of the present invention have been detected;

(iv) crossing the selected individual with a higher steviol glycoside content with another stevia plant;

(v) detecting the genetic features of the present invention from the genome of daughter plants obtained by crossing, (vi) measuring the content of steviol glycoside of the tissue of the daughter plants in which the genetic features of the present invention have been detected, (vii) selecting individuals having a higher steviol glycoside contentratio from among the daughter plants in which the genetic features of the present invention are detected.

Individuals with a high steviol glycoside content of choice may be, for example, up to 50%, up to 40%, up to 30%, up to 20%, up to 10%, up to 5%, up to 4%, up to 3%, up to 2%, or up to 1% of the test stevia plants in which the genetic features of the present invention have been detected, with respect to the high steviol glycoside content. Other stevia plants to be crossed may or may not contain the genetic feature(s) of the present invention. In the above embodiment, steps (iv) to (vii) can be repeated a plurality of times. In this way, stevia plants with a higher steviol glycoside content can be screened.

In the screening method of the present invention, the test stevia plant may be a natural plant or a non-transgenic plant. Non-transgenic plants are as described in the section relating to the plant of the present invention.

In the screening method of the present invention, the test stevia plant may include a stevia plant subjected to a mutagenesis treatment and a progeny plant thereof. The induction of a variation is as described in the section relating to the plant of the present invention, and includes treatment with a mutagen, treatment with radiation or irradiation with light, and the like.

The present invention also provides the primer sets described above or combinations thereof, for example, the primer sets described above in Tables 1 to 2; and combinations of the primer set(s) described above in Table 1 that detect the genetic features (1), and the primer set(s) described above in Table 2 that detect the genetic features (2). The present invention further provides a primer set capable of amplifying a region having a nucleotide sequence selected from the group consisting of SEQ ID NOs: 1, 2, 13 and 17 by PCR, for example, a primer set with a forward primer comprising a nucleotide sequence of SEQ ID NO: 3, and a reverse primer comprising a nucleotide sequence of SEQ ID NO: 4; and a primer set with a forward primer comprising a nucleotide sequence of SEQ ID NO: 5, and a reverse primer comprising a nucleotide sequence of SEQ ID NO: 6. Furthermore, the present invention provides a combination of a primer set capable of amplifying a region having a nucleotide sequence of SEQ ID NO: 1 or 13 by PCR, and a primer set capable of amplifying a region having a nucleotide of SEQ ID NO: 2 or 17 by PCR, for example, a combination of a primer set with a forward primer comprising a nucleotide sequence of SEQ ID NO: 3, and a reverse primer comprising a nucleotide sequence of SEQ ID NO: 4; and a primer set with a forward primer comprising a nucleotide sequence of SEQ ID NO: 5, and a reverse primer comprising a nucleotide sequence of SEQ ID NO: 6.

In addition, the present invention provides a probe capable of detecting the presence and/or absence of the genetic features of the present invention, which may be referred to as the "probe of the present invention" hereinafter. The probe of the present invention may have a structure suitable for various detection methods (e.g., realtime PCR method such as TaqMan PCR method and the like) for the presence and/or absence of the genetic feature(s) of the present invention. For example, the probe of the present invention may comprise a nucleotide sequence complementary to a portion of a genome comprising a site related to the genetic feature of the present invention. Non-limiting examples of such probes include those comprising a sequence complementary to a nucleotide sequence selected from SEQ ID NOs: 7 to 12, 14 to 16 and 18 to 20. Of these sequences, SEQ ID NOs: 7 to 12 are specific for alleles related to the genetic feature of the present invention, and SEQ ID NOs: 14 to 16 and 18 to 20 are specific for alleles which are not the alleles related to the genetic feature of the present invention.

Further, SEQ ID NOs: 7 to 9 are specific for allele related to the genetic feature (1) of the present invention, and SEQ ID NOs: 10 to 12 are specific for allele related to the genetic feature (2) of the present invention. On the other hand, SEQ ID NOs: 14 to 16 are specific for an allele which is not the allele related to the genetic feature (1) of the present invention, and SEQ ID NOs: 18 to 20 are specific for an allele which is not the allele related to the genetic feature (2) of the present invention.

The presence of the genetic feature(s) of the present invention may be detected by detection of an allele related to the genetic feature of the present invention and/or undetection of an allele which is not an allele related to the genetic feature of the present invention, and the absence of the genetic feature(s) of the invention by undetection of an allele related to the genetic feature of the present invention or by detection of an allele which is not an allele related to the genetic feature of the present invention. The probes of the present invention preferably have a label. Non-limiting examples of such labels include fluorescent labels, luminescent labels, radioactive labels, dyes, enzymes, quenchers, binding moieties with detectable labels, and the like. In a specific embodiment, the probe of the present invention has a polynucleotide comprising a nucleotide sequence complementary to a sequence selected from SEQ ID NOs: 7 to 12, 14 to 16 and 18 to 20 and a label.

The present invention also provides a kit comprising the above-mentioned primer set and a restriction enzyme appropriate therefor. In a specific embodiment, the kit of the present invention comprises a primer set comprising a combination of a forward primer and a reverse primer stated in the above Tables 1-2 and a restriction enzyme appropriate therefor.

The kit of the present invention also comprises a primer set capable of amplifying by PCR a region having a nucleotide sequence selected from the group consisting of SEQ ID NOs: 1, 2, 13 and 17, and the above-mentioned probe of the present invention appropriate therefor.

These primer sets, probes and kits can be used to detect the genetic feature(s) of the present invention, used in the screening methods of the present invention, and the like. These primer sets and kits may also comprise an instruction including an explanation on the detection of genetic feature (s) of the present invention and on the screening method of the present invention, e.g., a written instruction, information of a site comprising information regarding the method of use (e.g., URL and 2D code), and media, e.g., a flexible disk, a CD, a DVD, a Blu-ray disk, a memory card, a USB memory, etc., having recorded thereon information regarding the method of use, and the like.

In some embodiments, the present invention provides a screening kit for the high steviol glycoside-content stevia plant, comprising a reagent for detecting the presence and/or the absence of the genetic feature (1), and a reagent for detecting the presence and/or the absence of the genetic feature (2). The reagent may comprise a primer and/or a probe for use in CAPS method, dCAPS method or TaqMan PCR method. In a specific embodiment, the reagent for detecting the presence and/or the absence of the genetic feature (1) comprises a combination of a primer set and a restriction enzyme for detecting the above genetic feature (1) by the dCAPS method, for instance a combination of a primer set and a restriction enzyme stated in Table 1, or a combination of a primer set that amplifies the site(s) related to the genetic feature (1) (e.g., a site comprising a sequence selected from SEQ ID NOs: 7 to 9), and a probe having a nucleotide sequence complementary to a site related to the genetic feature (1), which can be used in the TaqMan PCR method or the like. In a specific embodiment, the reagent for detecting the presence and/or the absence of the genetic feature (2) comprises a combination of a primer set and a restriction enzyme for detecting the above genetic feature (2) by the dCAPS method, for instance a combination of a primer set and a restriction enzyme stated in Table 2, or a combination of a primer set that amplifies the site(s) related to the genetic feature (2) (e.g., a site comprising a sequence selected from SEQ ID NOs: 10 to 12), and a probe having a nucleotide sequence complementary to a site related to the genetic feature (2), which can be used in the TaqMan PCR method or the like.

4. Method of Producing Extract Derived from Plant and Product Comprising the Extract In a further aspect, the present invention provides a method of producing an extract comprising a steviol glycoside (e.g., RebD and/or RebM), comprising a step of obtaining an extract from the plant of the present invention, a stevia plant selected by the screening method of the present invention or a stevia plant produced by the production method of the present invention, or a seed, a leaf (e.g., dried leaf or fresh leaf), a tissue, a tissue culture or a cell of the plant (hereinafter, may be referred to as the "extract production method of the present invention").

Further provided is an extract comprising a steviol glycoside (e.g., RebD and/or RebM) from the plant of the present invention, a stevia plant selected by the screening method of the present invention or a stevia plant produced by the production method of the present invention, or a seed, a leaf (e.g., dried leaf or fresh leaf), a tissue, a tissue culture or a cell of the plant (hereinafter, may be referred to as the "extract of the present invention"). The extract of the present invention is preferably produced by the extract production method of the present invention. Furthermore provided is a method of producing a steviol glycoside, comprising a step of purifying a steviol glycoside (e.g., RebD and/or RebM) from the extract of the present invention (hereinafter, may be referred to as the "steviol glycoside production method of the present invention"). The steviol glycoside production method of the present invention may further comprise a step of obtaining an extract comprising a steviol glycoside from the stevia plant of the present invention, a stevia plant selected by the screening method of the present invention or a stevia plant produced by the production method of the present invention.

The extract comprising a steviol glycoside can be obtained by reacting a fresh leaf or a dried leaf of the plant of the present invention with a suitable solvent (an aqueous solvent such as water or an organic solvent such as an alcohol, ether or acetone). For the extraction conditions, etc., see a method described in Ohta et al., supra or WO2010/038911, or a method described in Examples mentioned later.

Each steviol glycoside can be purified from the extract comprising a steviol glycoside by use of a method known in the art such as a gradient of ethyl acetate or any of other organic solvents: water, high performance liquid chromatography (HPLC), gas chromatography, time-of-flight mass spectrometry (TOF-MS), or ultra (high) performance liquid chromatography (UPLC). Examples of the steviol glycoside are as described in the section relating to the plant of the present invention.

One embodiment of the extract obtained by the extract production method of the present invention (hereinafter, referred to as the "extract of the present invention") comprises a steviol glycoside at higher content as compared with an extract obtained from a stevia plant not having the genetic feature of the present invention.

The extract of the present invention may comprise a steviol glycoside at a content higher by 5% or more, 6% or more, 7% or more, 8% or more, 9% or more, 10% or more, 11% or more, 12% or more, 13% or more, 14% or more, 15% or more, 16% or more, 17% or more, 18% or more, 19% or more, 20% or more, 21% or more, 22% or more, 23% or more, 24% or more, 25% or more, 26% or more, 27% or more, 28% or more, 29% or more, 30% or more, 31% or more, 32% or more, 33% or more, 34% or more, 35% or more as compared with an extract obtained from a stevia plant not having the genetic feature of the present invention. The extract of the present invention and the extract obtained from the stevia plant not having the genetic feature of the present invention may be those obtained by the same process.

The extract of the present invention thus obtained and/or a purified steviol glycoside (e.g., RebD and/or RebM) obtained by the method of producing purified steviol glycoside of the present invention can be mixed with other component(s) to produce a food or beverage, sweetener composition, flavor or medicament comprising a steviol glycoside. Accordingly, in an alternative aspect, the present invention provides a method of producing a food or beverage, a sweetener composition, a flavor or a medicament, comprising a step of mixing the extract of the present invention, and/or a purified steviol glycoside obtained by the method of producing purified steviol glycoside of the present invention with other component(s). The present invention further provides a food or beverage, sweetener composition, flavor or medicament comprising a steviol glycoside, obtained by the production method. In this context, the food or beverage comprises a beverage and a food. Thus, in a certain embodiment, the present invention provides a beverage, food, sweetener composition, flavor or medicament and also provides a method of producing the beverage, food, sweetener composition, flavor or medicament.

5. Nucleotide Sequence Relating to Plant of Present Invention

In another aspect, the present invention provides nucleotide sequences relating to the stevia plant of the present invention.

A nucleotide sequence relating to a stevia plant having the genetic feature (1) comprises or consists of a nucleotide sequence selected from SEQ ID NOs: 1, 7, 8 and 9. A nucleotide sequence relating to a stevia plant having the genetic feature (2) comprises or consists of a nucleotide sequence selected from SEQ ID NOs: 2, 10, 11 and 12. A nucleotide sequence relating to a stevia plant having the genetic features of the present invention comprises or consists of a combination of a nucleotide sequence selected from SEQ ID NOs: 1, 7, 8 and 9 and a nucleotide sequence selected from SEQ ID NOs: 2, 10, 11 and 12.

EXAMPLES

Hereinafter, the present invention will be described with reference to Experimental Examples, Examples, etc. However, the present invention is not limited by these specific embodiments.

(1) Generation of Population with High Steviol Glycoside Content

A wild type stevia species (commercially available variety) was treated with ethyl methanesulfonate (EMS), and the resultant was seeded and cultivated in a greenhouse within the Suntory World Research Center. An appropriate amount of fresh leaves was sampled from each grown individual, and the concentration of steviol glycoside was quantitatively determined by LC-MS/MS (Shimadzu LCMS8050). Specifically, 0.25 g of the fresh leaves was dried by freeze drying, and 0.05 g of homogenized dry matter thereof was added into a 100-fold amount (5 mL) of pure water.

Extraction by ultrasonic treatment for 20 minutes, and centrifugation and filtration were performed, followed by 60-fold dilution with 32% acetonitrile to obtain a liquid sample. The concentration of RebA, RebB, RebC, RebD, RebF, RebM, RebN, RebO and stevioside was quantitatively determined by LC/MS-MS analysis on this 1 mL of liquid sample in a LCMS8050 MRM mode, and individuals having the total concentration of about 5 to 20% were selected and crossed to obtain seeds. Such selection was repeated over four generations to obtain Population A.

(2) Gene Analysis of High Steviol Glycoside-Content Individuals

An appropriate amount of fresh leaves was sampled from each individual of Population A, and the concentrations of RebA, RebB, RebC, RebD, RebE, RebF, RebG, RebM, RebN and stevioside (TSG) were quantitatively determined by LC/MS-MS (Shimadzu LCMS8050) in the same way as in the preceding section (1). Also, genomic DNA was extracted from the fresh leaves of some individuals, and genetically analyzed using a sequencer (HiSeq 2500, Illumina, Inc.). As a result, the average TSG content of the individual group having the genetic features of the present invention were found to tend to be higher than the average TSG contents of individual that did not have the genetic features of the present invention, all the individuals of Population A, and the individuals having the genetic features (2). Accordingly, in order to efficiently detect the genetic features, dCAPS primers for detecting the genetic features (1) and (2) were generated, and the remaining individuals were evaluated for the presence or absence of these genetic features by the dCAPS method.

The following dCAPS primers and restriction enzymes were used.

genetic feature (2) which is homozygous or heterozygous was determined as having the genetic features.

TABLE 3

Sequence of dCAPS primers and restriction enzyme

| Genetic feature | Forward primer | Reverse primer | Restriction enzyme |
|---|---|---|---|
| (1) | GGCAGCCATTGATGATGTTG TTGAA (SEQ ID NO: 21) | CCAATTCTCATAGAAAATA TGATAGAATAAATGCGT (SEQ ID NO: 22) | RsaI |
| (2) | TTATTTAATGATCCAATGGAG GGGGTGATTCAGGTAATAAA AGGCACT (SEQ ID NO: 25) | TGAGGGTTCTCAATTGAT TTCCGATTGG (SEQ ID NO: 28) | SpeI |

The detection of each genetic feature by the dCAPS method was performed as follows. First, genomic DNA was extracted from the fresh leaves of each individual, and PCR was performed using the above dCAPS primers for each genetic feature. The above restriction enzyme for each genetic feature was added to the PCR product, and enzymatic reaction was performed at 37° C. The restriction enzyme-treated products were electrophoresed using a microchip type electrophoresis apparatus LabChip GX Touch HT (PerkinElmer, Inc.). The presence or absence of the genetic feature was determined on the basis of the obtained band pattern. Specifically, an individual for which only a band of a degradation product was found as to the genetic feature (1) which is homozygous was determined as having the genetic features, while an individual for which a band of a non-degradation product was found as to the From the results shown in Table 4 and FIG. 3, the tendency found by sequencing was confirmed. Specifically, the average TSG content of the individual group having the genetic features of the present invention was higher by 43.5%, 27.4% and 7.2% than those of the individuals that does not have the genetic features of the present invention, all the individuals in Population A and the individuals having the genetic feature (2), respectively. Although the genetic feature (2) is known as a marker for the selection of a high sweet component content stevia plant (Patent Literature 3), it is 5 evident that its combination with the genetic feature (1) of the present invention can select an individual with higher TSG content.

TABLE 4

Relationship between TSG content and genetic features

|  | All individuals | Individuals having genetic feature (1) | Individuals having genetic features (1) and (2) | Individuals having neither genetic feature (1) nor genetic feature (2) |
|---|---|---|---|---|
| TSG (%) | 11.99 | 14.26 | 15.28 | 10.65 |

INDUSTRIAL APPLICABILITY

The present invention enables the more efficient provision of Steviol glycoside and can therefore provide a food or beverage, a sweetener composition, a flavor or a medicament, etc. having good quality of taste by comprising sufficient amount of Steviol glycoside.

The invention claimed is:

1. A method of screening for a high steviol glycoside-content stevia plant, comprising detecting from the genome of a test stevia plant the presence and/or the absence of the following genetic features (1), and the presence and/or the absence of the following genetic features (2):
    (1) homozygous for the allele wherein the base at the position corresponding to position 290 of SEQ ID NO: 1 is T; and
    (2) homozygous or heterozygous for the allele wherein the base at the position corresponding to position 40 of SEQ ID NO: 2 is A.

2. The method according to claim 1, further comprising measuring the content of steviol glycoside in a test stevia plant tissue in which the presence and/or the absence of the genetic features has/have been detected.

3. The method according to claim 1, wherein the steviol glycoside content of the high steviol glycoside-content stevia plant is higher by 3% or more than that of a stevia plant selected by a screening method comprising detecting the presence and/or the absence of the genetic features (2) but not comprising detecting the presence and/or the absence of the genetic features (1).

4. The method according to claim 1, wherein the detecting the presence and/or the absence of the genetic features is performed by use of dCAPS method or TaqMan PCR method.

5. A screening kit for a stevia plant with high steviol glycoside content, comprising a reagent for detecting the presence and/or the absence of the following genetic features (1), and a reagent for detecting the presence and/or the absence of the following genetic features (2):
    (1) homozygous for the allele wherein the base at the position corresponding to position 290 of SEQ ID NO: 1 is T; and
    (2) homozygous or heterozygous for the allele wherein the base at the position corresponding to position 40 of SEQ ID NO: 2 is A.

6. The kit according to claim 5, wherein the reagent comprises a primer and/or a probe for use in CAPS method, dCAPS method or TaqMan PCR method.

7. A high steviol glycoside-content stevia plant having the following genetic features (1) and (2):
    (1) homozygous for the allele wherein the base at the position corresponding to position 290 of SEQ ID NO: 1 is T; and
    (2) homozygous or heterozygous for the allele wherein the base at the position corresponding to position 40 of SEQ ID NO: 2 is A.

8. The plant according to claim 7, wherein the plant is a non-genetically modified plant.

9. The plant according to claim 7, wherein the plant includes a stevia plant subjected to a mutagenesis treatment and a progeny plant thereof.

10. A seed, a tissue, a dried leaf, a tissue culture or a cell of the plant according to claim 7.

11. The tissue, tissue culture or cell according to claim 10, which is selected from an embryo, a meristem cell, a pollen, a leaf, a root, a root apex, a petal, a protoplast, a leaf section and a callus.

12. A method of producing a high steviol glycoside-content stevia plant, the method comprising crossing the plant according to claim 7 with a second stevia plant.

13. The method according to claim 12, wherein the second plant is a high steviol glycoside-content stevia plant having the following genetic features (1) and (2):
    (1) homozygous for the allele wherein the base at the position corresponding to position 290 of SEQ ID NO: 1 is T; and
    (2) homozygous or heterozygous for the allele wherein the base at the position corresponding to position 40 of SEQ ID NO: 2 is A.

14. A method of producing the high steviol glycoside-content stevia plant according to claim 7, comprising modifying the genome of a stevia plant such that the genome has the following genetic features (1) and (2):

(1) homozygous for the allele wherein the base at the position corresponding to position 290 of SEQ ID NO: 1 is T; and
(2) homozygous or heterozygous for the allele wherein the base at the position corresponding to position 40 of SEQ ID NO: 2 is A.

15. The method according to claim 14, wherein the modification of the genome is performed by a mutagenesis treatment.

16. A method of producing an extract comprising a steviol glycoside at a high content, comprising:
providing the plant according to claim 7 or the seed, tissue, dried leaf, tissue culture or cell thereof; and
obtaining an extract from the plant, seed, tissue, dried leaf, tissue culture or cell.

17. A method of producing steviol glycoside, comprising:
providing the plant according to claim 7 or the seed, tissue, dried leaf, tissue culture or cell thereof;
obtaining an extract from the plant, seed, tissue, dried leaf, tissue culture or cell; and
purifying steviol glycoside from the extract.

18. A method of producing a food or beverage, a sweetener composition, a flavor or a medicament, comprising:
providing the plant according to claim 7 or the seed, tissue, dried leaf, tissue culture or cell thereof;
obtaining an extract from the plant, seed, tissue, dried leaf, tissue culture or cell; and
adding the extract to a raw material for the food or beverage, sweetener composition, flavor or medicament.

* * * * *